US00PP33881P2

(12) United States Plant Patent
Van Swieten

(10) Patent No.: US PP33,881 P2
(45) Date of Patent: Jan. 18, 2022

(54) ***PHALAENOPSIS* ORCHID PLANT NAMED 'PHA1277660'**

(50) Latin Name: ***Phalaenopsis* hybrid**
Varietal Denomination: PHA1277660

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,681

(22) Filed: Sep. 22, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHA1277660', particularly characterized by having white, shaded, and flecked flowers with purplish-red lips, flowers that are convex in lateral view, dorsal sepals with an incurving curvature of the longitudinal axis, lateral lobes with medium curvature, and is propagated by meristem tissue culture, is disclosed.

3 Drawing Sheets

Genus and species: *Phalaenopsis* hybrid.
Variety denomination: 'PHA1277660'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA1277660'.

The new *Phalaenopsis* plant is a product of a planned breeding program conducted by the inventor in Bleiswijk, the Netherlands. The objective of this breeding program was to create a new *Phalaenopsis* plant with attractive, white, shaded, and flecked, medium-sized flowers with purplish-red lips, suitable for potted plant production.

The new *Phalaenopsis* plant 'PHA1277660' is a result of cross-pollination made by the inventor in August 2013 in Bleiswijk, the Netherlands, of the proprietary female, or seed parent, *Phalaenopsis* hybrid '01-3358' (unpatented) with the proprietary male, or pollen parent, *Phalaenopsis* hybrid '01-4564' (unpatented).

The new *Phalaenopsis* was selected by the inventor as a single plant within the progeny of the stated cross-pollination in a controlled greenhouse in Bleiswijk, the Netherlands, in June 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 22, 2020 (Application no. 2020/2304), by Applicant who obtained the subject matter disclosed directly from the inventor. 'PHA1277660' has not been made publicly available or sold anywhere in the world prior to the effective filing date of this application with the exception of sales or disclosures made one year or less before the effective filing date of this claimed invention by Applicant who obtained 'PHA1277660' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA1277660' as a new and distinct variety of *Phalaenopsis* plant:

1) White, shaded, and flecked flowers with purplish-red lips (intensity and number of flecks depend on temperature during growing period);
2) Flower shape in lateral view is convex;
3) Curvature of longitudinal axis of dorsal sepal is incurving; and
4) Curvature of lateral lobe is medium.

DESCRIPTION OF THE PHOTOGRAPHS

This new *Phalaenopsis* plant is illustrated by the accompanying photographs which show the overall plant habit including blooms, bud, and foliage of the plant; the colors shown are as true as can be reasonably obtained by conventional photographic procedures. The photographs were taken in a greenhouse in Bleiswijk, the Netherlands, from 50-week-old plants in July 2021. Colors in the photographs may differ from the color values cited in the detailed botanical description, which accurately describe the actual colors of the new variety.

DESCRIPTION OF THE NEW VARIETY

Figure 1:
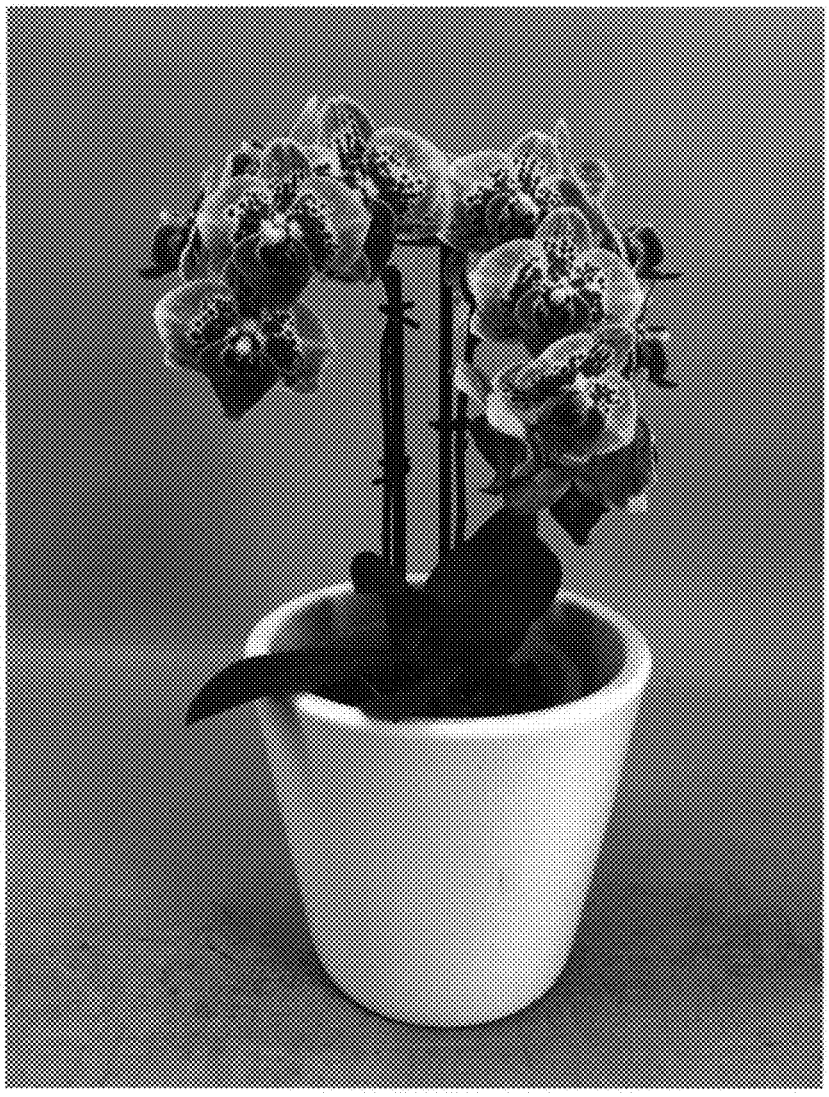
FIG. 1 shows the overall plant habit, including blooms, bud, and foliage of 'PHA1277660'.
Figure 2:
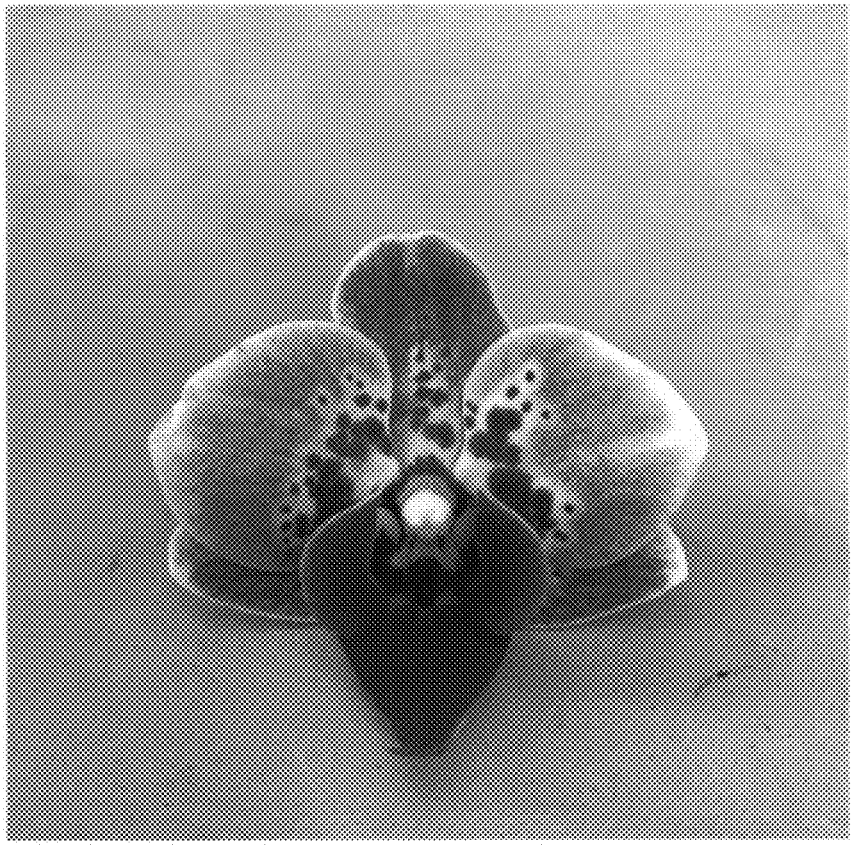
FIG. 2 shows a close-up of a flower of 'PHA1277660'.
Figure 3:
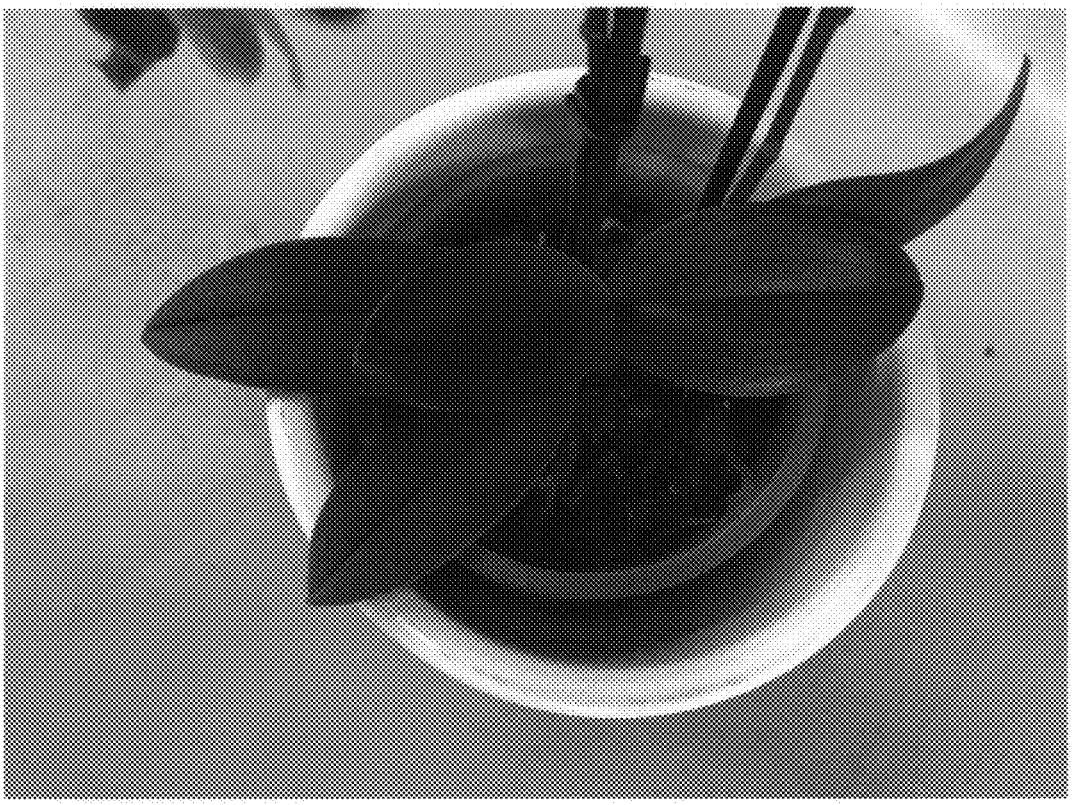
FIG. 3 shows an overhead view of the leaves of 'PHA1277660'.

The following detailed description sets forth the distinctive characteristics of 'PHA1277660'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in July 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHA1277660'.

Parentage:
- *Female parent*.—*Phalaenopsis* cultivar '01-3358' (unpatented).
- *Male parent*.—*Phalaenopsis* cultivar '01-4564' (unpatented).

Propagation:
- *Type*.—Meristem tissue culture.

Roots:
- *Root description*.—Greyed-green (a color in between RHS 190B and RHS 190C) colored roots with branching lateral roots having yellow-green (RHS 144C) colored root tips.

Plant:
- *Crop time to flowering*.—Following asexual propagation (in vitro), the rooted cuttings grow for 20-24 weeks. After transplantation into 12-cm pots, the plants are finished after 48 to 50 weeks.
- *Growth habit of the peduncle*.—Upright to slightly pendent with raceme inflorescence.
- *Height* (*from soil level to top of inflorescence*).—Approximately 20.0 cm to 30.0 cm.
- *Width* (*measured from leaf tips*).—About 20.0 cm to 22.0 cm.
- *Vigor*.—Strong.

Leaves:
- *Mature leaves*.—Quantity per plant: 6 to 7 leaves are produced before flowering. Length (fully expanded): 9.0 cm to 11.0 cm. Width: 3.5 cm to 4.5 cm. Position of the broadest part of the leaf: At the middle. Shape: Oblong. Base shape: Slightly elongated. Apex: Obtuse asymmetric. Leaf blade angle with the petiole (measured from the horizontal position): Between 10 degrees and 30 degrees. Leaf margin: Entire. Color: Upper surface: RHS 147A. Lower surface: RHS 147B. Texture (both upper and lower surfaces): Smooth. Thickness: 1.6 mm to 1.9 mm. Variegation: Absent. Venation: Pattern: Parallel. Color of the midvein: Upper surface: RHS 147A. Lower surface: RHS 146B.

Peduncle:
- *Quantity per plant*.—1 to 2.
- *Number of flowers per peduncle*.—10 to 14.
- *Length*.—20.0 cm to 30.0 cm.
- *Diameter*.—3.0 mm to 4.0 mm.
- *Strength*.—Strong.
- *Aspect*.—Upright to slightly pendent.
- *Texture*.—Smooth.
- *Color*.—Mix of yellow-green (RHS 147A and RHS 146A) with a hint of dark purplish-red (RHS N79A).
- *Internode length*.—1.5 cm to 2.5 cm.

Inflorescence description:
- *Appearance*.—Upright to slightly pendent, raceme inflorescence with bilaterally symmetrical flowers that open in succession beginning with the lowermost flower.
- *Number of inflorescences*.—1 to 2.
- *Inflorescence size*.—Height (from base to tip): 100.0 mm to 140.0 mm.
- *Flowering time*.—First flowers can be expected 10 to 11 months after planting in a 12-cm pot.
- *Flower*.—Height: 50.0 mm to 55.0 mm. Diameter: 53.0 mm to 58.0 mm. Depth of lip: 22.0 mm to 24.0 mm.
- *Flower shape*.—Convex.
- *Flower longevity*.—On the plant: 8 to 10 weeks.
- *Fragrance*.—Absent.
- *Flower bud*.—Average size: Medium. Length: 17.0 mm to 19.0 mm. Width: 15.0 mm to 17.0 mm. Shape: Egg shaped. Color: Yellow-green (RHS 146D) with diluting purple flecks (RHS N77A) and purplish-red shade (RHS N77B).
- *Petals*.—Arrangement: Open/free. Shape: Semi-circular. Apex: Obtuse asymmetric. Margin: Weakly undulated. Length (from base to tip): 24.0 mm to 26.0 mm. Width: 27.0 mm to 29.0 mm. Position of the broadest part of the petal: Toward the base. Color (when fully opened): Upper surface: Basic color: White (RHS NN155C). Over color: Dark red-purple flecks (a color in between RHS 187B and RHS N79C); light red-purple shade (a color in between RHS N78B and RHS N80B) toward apex. Lower surface: Basic color: White (RHS NN155C). Over color: Diluting dark purplish flecks (RHS N79B); purplish-pink shade (RHS N78C). Number of spots, flecks, and stripes on the petals (upper surface): Medium flecks. Color of spots, flecks, and stripes on the petals (upper surface): A color in between RHS 187B and RHS N79C. Density of netting of the petals (upper surface): None. Color of the netting (upper surface): Not applicable.
- *Dorsal sepal*.—Shape: Elliptic. Apex: Emarginated symmetric. Margin: Entire. Length (from base to tip): 27.0 mm to 29.0 mm. Width: 19.0mm to 21.0 mm. Position of the broadest part of the dorsal sepals: At the middle. Color (when fully opened): Upper surface: Basic color: White (RHS NN155C). Over color: Dark reddish-purple flecks (a color in between RHS 187B and RHS N79C); red-purple shade (a color in between RHS N78B and RHS N80B). Lower surface: Basic color: White (RHS NN155C). Over color: Light yellow-green (RHS 145C) at the base; purplish-red fleck (RHS N79B) at the base; light purple shade (RHS 76A) toward margin. Number of spots, flecks, and stripes on the dorsal sepals (upper surface): Medium flecks; few stripes. Color of spots, flecks, and stripes on the dorsal sepals (upper surface): Flecks (RHS N79B); stripes (RHS N78B). Density of netting of the dorsal sepals (upper surface): None. Color of the netting: Not applicable.

*Lateral sepals*.—Shape: Ovate. Apex: Obtuse asymmetric. Margin: Weakly undulated. Length (from base to tip): 27.0 mm to 29.0 mm. Width: 18.0 mm to 20.0 mm. Position of the broadest part of the lateral sepals: Toward the base. Color (when fully opened): Upper surface: Basic color: White (RHS NN155C). Over color: Touch of light yellow (RHS 145C) and dark reddish-purple flecks (a color in between RHS N79B and RHS N79C) at the base; reddish-purple stripes (RHS N78B) and purplish-pink shade (RHS N78C) toward the tip. Lower surface: Basic color: White (RHS NN155C). Over color: Diluting dark purplish-red flecks (RHS N79B); light yellow-green (RHS 145C) and light purple shade (RHS 76A) toward the tip. Number of spots, flecks, and stripes on the lateral sepals (upper surface): Medium to many flecks; few to medium stripes. Color of spots, flecks, and stripes on the lateral sepals (upper surface): Flecks (a color in between RHS N79B and RHS N79C); stripes (RHS N78B). Density of netting of the lateral sepals (upper surface): None. Color of the netting (upper surface): Not applicable.

*Labellum* (*lip*).—Whiskers: Present. Length of whiskers: 2.0 mm to 3.0 mm. Color of whiskers: Reddish-purple (RHS N78B) with white tips (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated (widely wavy). Length: 16.0 mm to 18.0 mm. Width: 11.0 mm to 13.0 mm. Color: Upper surface: Touch of greenish-yellow (RHS 6A) with dark red fleck (RHS 187B) at the base; white (RHS NN155C) and red (RHS 185A) toward margin on one side; purplish-red (RHS 71A) and reddish-purple (RHS N78A) toward margin on the other side and the tip. Lower surface: Yellowish-white (RHS 6B) at the base; red margin (RHS 185B) and white (RHS NN155C) on one side; reddish-purple (RHS N78B) toward the other margin and the tip. Number of spots, flecks, and stripes on the lateral lobe: One fleck. Color of spots, flecks, and stripes on the lateral lobe: RHS 187B. Density of netting of the lateral lobe: None. Color of the netting: Not applicable.

*Apical lobe*.—Shape: Triangular. Margin: Entire. Length: 16.0 mm to 18.0 mm. Width: 19.0 mm to 21.0 mm. Color: Upper surface: Touch of dark reddish-orange (RHS 175B) at the base; purplish-red (RHS 71A) and reddish-purple (RHS N78A) toward whiskers. Lower surface: Dark reddish-orange (RHS 175C) toward wings; light yellow-green (RHS 157C) at the base; reddish-purple (RHS N78A) on sides toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Small. Height: 4.0 mm to 5.0 mm. Length: 3.0 mm to 4.0 mm. Width: 3.0 mm to 4.0 mm. Color: Greenish-white (RHS 155C) on sides; yellow front and tips (RHS 162B); dark red-brown flecks (mix of RHS 200B and RHS 187A).

Reproductive organs:

*Column*.—Length: 8.0 mm to 11.0 mm. Diameter: 4.1 mm to 4.5 mm. Color: White (RHS NN155C) at the base and toward the tip and purplish-pink (RHS N78C) at the middle.

*Pollinia*.—Quantity: 2. Diameter: 0.9 mm to 1.1 mm. Color: Orange-yellow (RHS 23A).

*Ovary*.—Length: 9.0 mm to 11.0 mm. Diameter: 1.5 mm to 1.7 mm.

*Pedicel*.—Length: 30.0 mm to 32.0 mm. Diameter: 1.8 mm to 2.0 mm. Color: Dark purplish-red (RHS N79A) at the base; yellow-green (RHS 144B) and light yellow-green (RHS 145B) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA1277660' differs from the female parent plant '01-3358' (unpatented) in that 'PHA1277660' has flowers with a shaded and flecked pattern that are convex in lateral view, whereas '01-3358' has flowers with a shaded and striped pattern that are flat in lateral view.

'PHA1277660' differs from the male parent plant '01-4564' (unpatented) in that 'PHA1277660' has flowers that are convex in lateral view and leaves that are short in length, whereas '01-4564' has flowers that are concave in lateral view and leaves that are medium in length.

'PHA1277660' is most similar to the commercial *Phalaenopsis* plants named 'PHALGYQAN' (U.S. Plant Pat. No. 30,276) and 'PHALFEQBIN' (U.S. Plant Pat. No. 29,615). 'PHA1277660' differs from the commercial variety 'PHALGYQAN' in that 'PHA1277660' has triangular apical lobes, whereas 'PHALGYQAN' has ovate apical lobes. Additionally, 'PHA1277660' has longer dorsal sepals, narrower leaves, and wider lateral lobes than 'PHALGYQAN'.

'PHA1277660' differs from the commercial variety 'PHALFEQBIN' in that 'PHA1277660' has flowers that are convex in lateral view, whereas 'PHALFEQBIN' has flowers that are flat in lateral view. Additionally, 'PHA1277660' has shorter whiskers, shorter dorsal sepals, and narrower leaves than 'PHALFEQBIN'.

I claim:

1. A new and distinct variety of *Phalaenopsis* plant named 'PHA1277660', substantially as described and illustrated herein.

* * * * *